ed Dec. 1988.
United States Patent [19]
Blom et al.

[11] Patent Number: 5,064,433
[45] Date of Patent: Nov. 12, 1991

[54] VOICE PROSTHESIS INSERTION ASSEMBLIES

[75] Inventors: Eric D. Blom, Indianapolis, Ind.; Frederick L. Coe, Santa Barbara, Calif.

[73] Assignee: Helix Medical, Inc., Santa Barbara, Calif.

[21] Appl. No.: 487,782

[22] Filed: Mar. 5, 1990

[51] Int. Cl.⁵ .............................................. A61B 1/00
[52] U.S. Cl. .................................... 623/9; 128/207.16
[58] Field of Search .......... 623/9; 128/207.16, 207.17, 128/207.29

[56] References Cited

U.S. PATENT DOCUMENTS

| 4,435,853 | 3/1984 | Blom et al. | 128/207.16 |
| 4,614,516 | 9/1986 | Blom et al. | 623/9 |
| 5,016,614 | 5/1991 | MacAllister | 128/207.14 X |

FOREIGN PATENT DOCUMENTS 0093567 11/1983 European Pat. Off. ................ 623/9

OTHER PUBLICATIONS

"Tracheoesophaged Valves: Problems, Solutions, and Directions for the Future", presented Jun. 4, 1988, published Dec. 1988.
*Head and Neck Surgery Supplement II*, pp. S142–S145 by Dr. Eric Blom.

*Primary Examiner*—David J. Isabella
*Assistant Examiner*—Elizabeth M. Burke
*Attorney, Agent, or Firm*—Marvin E. Jacobs

[57] ABSTRACT

A voice prosthesis insertion assembly is described including a voice prosthesis device and a placement tool for positioning the device in a fistula connecting a trachea and anesophagus of a laryngectomized patient. The voice prosthesis device has an attachment means formed thereon and the placement tool has an attachment means molded integrally and homogeneously thereon for detachably interconnecting the device with the tool. As a result of this construction, a positive interconnection of the voice prosthesis device and the placement tool is maintained during positioning of the device in the fistula and such interconnection may be maintained until detachment is desired.

18 Claims, 2 Drawing Sheets

VOICE PROSTHESIS INSERTION ASSEMBLIES

DESCRIPTION

1. Technical Field

This invention relates generally to voice prosthesis assemblies for inserting a voice prosthesis device into a surgical fistula communicating between the trachea and the esophagus of a laryngectomized patient. More particularly, the invention relates to assemblies including a voice prosthesis device within the fistula and further including means integrally and homogeneously molded on a placement tool for mechanically retaining the voice prosthesis device on the placement tool in order to facilitate the positioning of the device in the fistula.

2. Discussion of Prior Art

A variety of tubular voice prosthesis devices for use in artificially created tracheo-esophageal fistulae are known. Exemplary of such devices are those popularly known as the Blom-Singer "Duckbill" prosthesis, the Blom-Singer Low Pressure prosthesis and the Panje prosthesis. Placement tools are also well known which consist of a rigid rod of thermoplastic material to be inserted into the central lumen of a prosthesis to rigidify the prosthesis sufficiently to insert it through a tracheostoma. Exemplary of the prior art prosthesis devices and placement tools therefor are those disclosed in U.S. Pat. Nos. 4,435,853; 4,586,931; 4,610,691; 4,614,516 and 4,773,412.

However, these previously described assemblies have presented a continuing problem in regard to the potential for premature detachment of the voice prosthesis device from the placement tool during insertion of the device into the fistula. For example, in order to insert the prior devices, the person inserting the device was required to perform a relatively awkward manual manipulation of a retention tab projecting outwardly from the surface of the prosthesis device, sometimes requiring use of both hands, to hold the retention tab and press it against the shaft of the prosthesis while inserting the device through the tracheostoma to the fistula. This action required a relatively high degree of manual dexterity which an elderly or ailing patient might not possess if he was required to insert or remove the prosthesis by himself.

Furthermore, with the prior assemblies an accidental slip of the hand or other mishap during the insertion operation would cause the detachment of the voice prosthesis device from the placement tool, which, in turn, could result in the prosthesis device contacting a contaminated surface whereas the device must be clean and disinfected when inserted in the fistula. Even more seriously, if the prosthesis device would disengage from the placement tool during insertion, it would be possible for the device to be lost into the trachea.

Statement of the Invention

The present invention provides an assembly for positively retaining a prosthesis on a placement tool until detachment is desired. The assembly of the invention detachably interconnects a voice prosthesis device with a placement tool. Additionally, the assemblies of the invention have the ability to mechanically retain the voice prosthesis device on the placement tool during insertion in order to overcome the above identified problems.

The invention is in the form of an assembly including a voice prosthesis device and a placement tool for positioning the voice prosthesis device in a fistula connecting the trachea and the esophagus of a patient having a total laryngectomy and resultant tracheostoma. The voice prosthesis device includes a cylindrical housing having a proximal or tracheal end and a distal or esophageal end with a channel therein connecting these ends for permitting the passage of air from the tracheostoma to the esophagus after the device has been positioned in the fistula. Attached to the proximal end of the housing is a tab or strap which extends generally radially outward from the axis of the housing and is intended to aid and assist in retaining the voice prosthesis device in the fistula. Additionally, the housing has a valve means positioned therein for controlling the passage of air through the channel in the housing. The placement tool includes an elongated housing having a handle at a first end thereof and a placement portion on a second end opposite the first end. The placement portion of the tool is shaped for insertion within the cylindrical housing of the voice prosthesis device to position the device in the fistula.

The improved voice prosthesis insertion assemblies in accordance with the present invention provide means for mechanically retaining the voice prosthesis device on the placement tool in order to avoid problems which may occur if the device and the tool become disengaged during the insertion and positioning of the device in a fistula. In this regard, the voice prosthesis device includes a connecting or mating section adapted for interconnection with a reciprocal connecting or mating section on the placement tool so that the voice prosthesis device and the placement tool can be effectively joined in a unitary assembly as the device is being inserted into the fistula. It is preferred that the connecting section on the voice prosthesis device comprise an attachment means formed on the radially outwardly extending tab or retention means thereof and the reciprocal connecting section on the placement tool comprise another attachment means integrally and homogeneously molded on the placement tool positioned intermediate the longitudinal end of the tool. Most preferably, the attachment means on the device and on the tool are compatibly shaped, for example, in the form of a hole, a rod or a post and these shapes are positioned on the device and the tool in a manner such that positive, but detachable, interconnection of the voice prosthesis device with the placement tool is achieved until detachment is desired.

These and other features and attendant advantages of the present invention will become more fully apparent as the invention becomes better understood from the following detailed description of preferred embodiments of the invention when read in conjunction with the accompanying drawings.

DETAILED DESCRIPTION OF THE INVENTION

Figure 1:
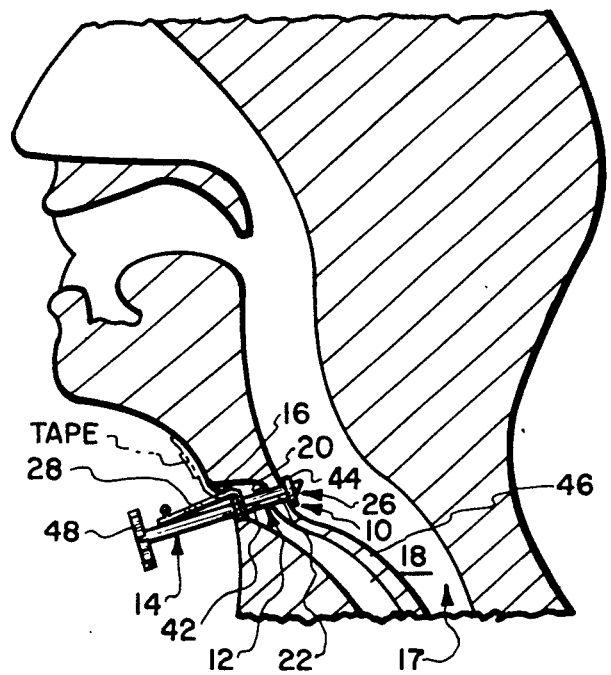
FIG. 1 is a schematic view showing an assembly in accordance with the present invention being employed to position a voice prosthesis device in a patient and further depicting in outline form the taping of a tab on the voice prosthesis device to the neck of the patient to retain the device in position after the tab is detached from an insertion tool.

Referring now to the drawings wherein like numerals have been used to designate the same or similar parts, FIG. 1 shows a voice prosthesis insertion assembly 10 in accordance with the present invention including a voice prosthesis device 12 and a placement or insertion tool 14. As illustrated in FIG. 1, the device 12 is inserted through a tracheostoma 16 and is properly positioned by a patient having a total laryngectomy within a surgical connection between the trachea 17 and the esophagus 18 known as a fistula 20.

Figure 2:
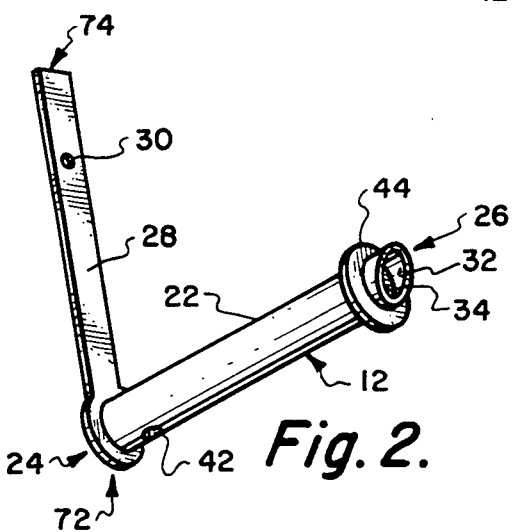
FIG. 2 is a perspective view of the voice prosthesis device shown in FIG. 1.

As shown in FIG. 2, the voice prosthesis device 12 includes an elongated tubular housing 22 which is constructed and composed of a medical grade silicone material having a proximal or tracheal end 24 and a distal or esophageal end 26. Although the housing 22 has been illustrated as being right circular cylindrical in cross section, other cross sectional shapes such as right elliptical cylindrical, can be employed. Mounted to the proximal end 24 is a retention means in the form of a single generally vertically upwardly projecting tab or strap 28 having an attachment means in the form of a hole 30 therein which enables the interconnection of the voice prosthesis device 12 and the placement tool 14 during insertion of the device 12, as will be described hereinafter. As will likewise be described in greater detail hereinafter, after insertion of the device 12 in the fistula 20, the tab 28 may be taped to the neck of the patient, as depicted in outline in FIG. 1, to assist in retaining and maintaining the voice prosthesis device 12 in the fistula 20.

If further security in retaining the prosthesis is desired, a hole can be provided in the tab 28 and a stitch can be taken through the hole in the tab and the tape.

Figure 5:
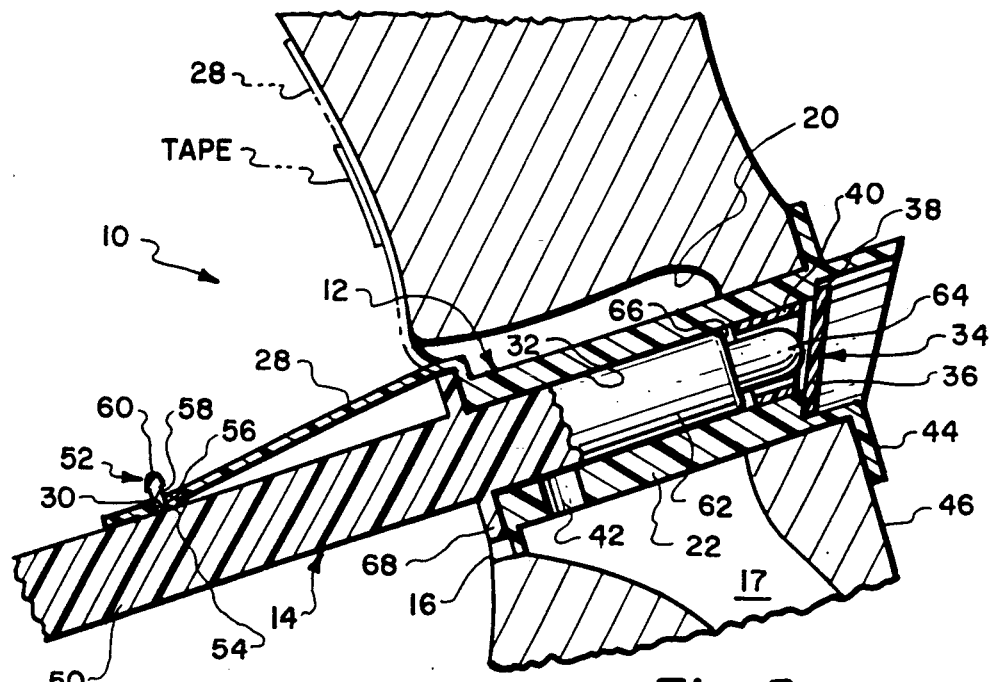
FIG. 5 is an enlarged longitudinal sectional view through an assembly in accordance with the present invention illustrating a voice prosthesis device detachably interconnected with a placement tool while the voice prosthesis device is being positioned in a fistula and further depicting in outline the attachment of the retention tab to the neck of the patient after disengagement of the tab from interconnection with the placement tool.

When inserted in the fistula 20, the distal end 26 of the elongated tubular housing 22 extends into the esophagus 18 so that the housing 22 having a channel 32 therein provides a passageway from the tracheostoma 16 to the esophagus 18. The elongated tubular housing 22 has a valve means in the form of a one-way valve 34 positioned within channel 32 including a valve membrane 36 hinged on the interior of the cylindrical housing 22 and adjacent to a valve seat 38 provided within the housing 22. The valve seat 38 cooperates with the hinged valve membrane 36 to permit the passage of air from the tracheostoma 16 or the trachea 17 into the esophagus 18 through the channel 32 in housing 22 and to block the flow of material from the esophagus 18 into the trachea 17. The air may enter the housing 22 through a port 42 positioned between the proximal end 24 of the housing 22 and the one-way valve 34 (FIGS. 2 and 5). However, this port 42 may be eliminated, if desired, since it has been found that airflow into the open proximal end 24 of housing 22 and through the valve 34 is sufficient to produce laryngeal speech.

It should be noted that although a particular form of valve arrangement has been illustrated, the specific valve arrangement to be employed herein is a matter of choice among a variety of known valve structures which may be substituted for the depicted construction within the scope of the present invention.

The cylindrical housing 22, as illustrated, also includes an annular abutment collar 40 for positioning the device 12 in a manner to be described hereinafter. The housing 22 further includes a retention collar 44 in the form of an annular flange. The retention collar 44 is positioned between the distal end 26 of the housing 22 and the port 42. The retention collar 44 aids in maintaining the position of the device 12 in the fistula 20 and in obtaining a seal when the voice prosthesis device 12 is seated in the fistula 20 as a result of the collar 44 abutting and engaging the esophageal side of the tracheoesophageal wall 46 to retain and hold the prosthesis device 12 in position. During insertion of the device 12 through a fistula 20, it has been observed that collar 44 snaps into position against the esophageal tissues when the device 12 has been properly positioned in the patient. When in such position, the device 12 is firmly retained in position and is not likely to become dislodged.

Figures 3, 4A:
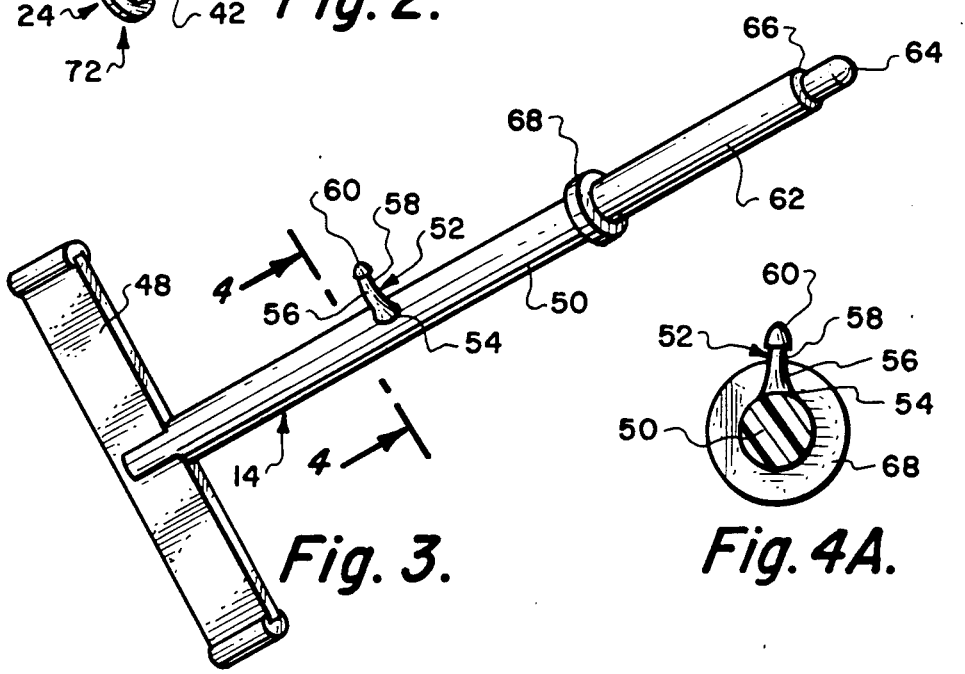
FIG. 3 is a perspective view of the placement tool shown in FIG. 1.
FIG. 4A is a front end view similar to that shown in FIG. 4 illustrating another embodiment of the attachment means in the form of a post projecting from the surface of the placement tool.

In FIG. 3, a placement tool 14 is shown which is particularly useful in engaging the voice prosthesis device 12 when the device 12 is inserted through the fistula 20 to connect the esophagus 18 and the tracheostoma 16. The placement tool 14 preferably includes an enlarged gripping or handle end 48, in a "T-shape" as illustrated which is adapted to be readily gripped or grasped within the fingers of the patient as the tool 14 is being used to position the voice prosthesis device 12 in the fistula 20.

Figure 4:
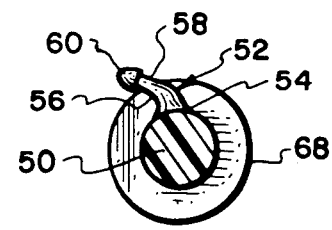
FIG. 4 is a front end view taken along section lines 4—4 of FIG. 3 illustrating an attachment means in the form of a post projecting from the surface of the placement tool.

The placement tool 14, also includes a placement end 50 having an attachment means thereon for interconnecting the voice prosthesis device 12 with the placement tool 14 during insertion of the device as will be described hereinafter. The attachment means on the placement tool 14 as illustrated herein in FIGS. 3, 4 and 4A is in the form of a post or other protuberance 52 molded integrally and homogeneously on the tool 14 projecting from the surface of the tool 14 intermediate the handle end 48 and the placement end 50 thereof. The post 52 includes a base section 54, an intermediate section 56 and an attachment end section 58 which is adapted for engagement and detachable interconnection with an attachment means on the voice prosthesis device 12 such as hole 30 in tab 28.

Base section 54, as best illustrated in FIGS. 4 and 4A, is a pedèstal having an enlarged circumferential dimension relative to the remaining portions of the post 52 and provides support and reinforcement for the outer sections of the post 52 thereby reducing the potential for the post to break off of the tool 14 in use. Section 56 connects the base 54 with the attachment end of the post 52 and provides a clearance space to accommodate the dimensional thickness of the attachment means on the voice prosthesis device 12 during interconnection. The attachment end section of post 52, preferably, is shaped to provide a positive interlock with the attachment means on the voice prosthesis device 12. For example, as best illustrated in FIGS. 4 and 4A, section 58 is in the form of a mechanical locking element 60 having a knob, a bead, a button or a conical shape or some other compatible shape which will mate with and detachably interlock with hole 30 in tab 28 on the voice prosthesis device 12.

Although the post 52 has been illustrated extending from the surface of the tool 14 at a generally acute angle in a plane transverse to the longitudinal axis of the tool 14 (FIGS. 3 and 4), it should be recognized that the angle of projection of the post 52 from the tool surface may vary. For example, in a preferred embodiment depicted in FIG. 4A, the post 52 projects vertically upwardly from the surface of tool 14 at a right angle relative to the longitudinal axis.

The placement end 50 of the tool 14 terminates in a projecting section 62 having a rounded, blunt end 64 extending outwardly from a shoulder section 66, the shoulder 66 being adapted to cooperate with and engage the abutment collar 40 upon insertion of the tool 14 into the device 12. Additionally, at a position intermediate the shoulder 66 and the post 52, the placement end of the tool 14 includes a collar or flange 68 which is adapted to cooperate with and to engage the proximal end 24 of the housing 22 upon insertion of the tool 14 into the device 12. Thus, when the projecting section 62 of the placement end 50 of the tool 14 is inserted into the channel 32 within the tubular housing 22 of the device 12, the collar 68 is positioned to engage the proximal end 24 of the device 12 and the shoulder 66 on the placement end 50 of the tool 14 is likewise positioned to engage collar 40 whereby the rounded, blunt end 64 on placement tool 14 is properly positioned without touching the valve membrane 36. This arrangement assures the protection of the sensitive valve components during insertion.

In operation, the voice prosthesis insertion assemblies 10 of the present invention are employed to expedite and facilitate the positioning of the voice prosthesis device 12 in the fistula 20 in the following manner. Initially, the attachment means on the tab 28 of the voice prosthesis device 12 is detachably interconnected with the attachment means on the placement tool 14. As best illustrated in FIG. 5, this interconnection is accomplished by passing the post 52 on the placement tool 14 through the hole 30 in the tab 28. Once the voice prosthesis device 12 and the tool 14 are engaged, the locking element or knob 60 on the attachment end 58 of the post 52 prevents the post from prematurely disengaging from the hole 30. Moreover, the tab 28 has been slightly elongated and is under tension which causes it to bind on the post and resist accidental detachment. Furthermore, the post 52 and the hole 30 are so dimensioned that detachment of the post from the hole may be achieved with a simple manual manipulation by the patient or other person positioning the device 12 in the fistula 20. Thus, the voice prosthesis device 12 and the placement tool 14 are effectively joined in a unitary assembly as the device 12 is being inserted into the fistula 20.

This ability of the present assemblies to retain the prosthesis device 12 positively on the placement tool 14 until detachment is desired is in contrast with prior assemblies which required the inserter of the prosthesis device such as the patient or the doctor to press the tab against the shaft of the tool, sometimes in an awkward manner possibly requiring use of both hands. This manual manipulation of the assembly during installation of the device resulted in the potential for the voice prosthesis device to detach prematurely and either come in contact with a contaminated surface such as a floor, or more seriously to be lost into the trachea of the patient. The improved assemblies of the present invention provide means for mechanically retaining the voice prosthesis device on the placement tool during insertion whereby such potential problems are eliminated.

Completion of the installation of the voice prosthesis device 12 is readily accomplished after the device has been positioned in the fistula 20 by detaching the post 52 on the insertion tool 14 from the hole 30 on the tab 28 which results in the disconnection of the voice prosthesis device 12 from interconnection with the placement tool 14. The placement tool 14 is then withdrawn from engagement with the device 12 and the tab 28 will reassume its normal generally vertical upwardly extending position from the proximal end of the device 12 which will enable its attachment to the neck of the patient, for example by taping the tab 28 to the patient's neck as illustrated in outline in FIGS. 1 and 5 herein. The attached tab 28 will assist in retaining and maintaining the voice prosthesis device 12 in proper alignment and position within the fistula 20.

Figure 6:
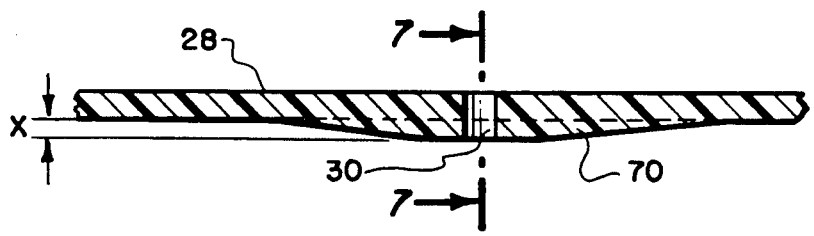
FIG. 6 is a sectional view through a portion of a retention tab on a voice prosthesis device illustrating another embodiment of the tab depicted in FIG. 5.
Figure 7:
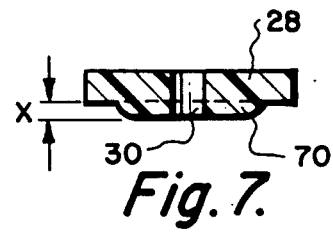
FIG. 7 is a section view taken along lines 7—7 in FIG. 6.

FIGS. 6–7 show a preferred embodiment of the tab 28 having a hole 30 formed therein as an attachment means. As illustrated, a reinforcement zone 70 is formed in the surface of the tab 28 about the circumference of the hole 30 by thickening the cross-section of the tab 28 in the zone 70 adjacent the hole 30 to an extent designated X in FIGS. 6–7. Preferably, the dimension of this added thickness X of the tab 28 is between about 0.010 and about 0.015 inch and, most preferably, about 0.013 inch.

The thickened reinforcement zone prevents the tab from tearing adjacent to hole 30 when the tab is stretched during insertion onto the post 52. The area surrounding the hole can be reinforced in other ways such as by adding fabric reinforcement to the tab during molding, laminating reinforcement fabric to either or both faces of the tab or by molding an annular insert into the tab to form the hole.

With regard to the dimension of the hole 30 in the tab 28 on the voice prosthesis device 12, it has been found that the diameter of the hole 30, preferably, should be slightly smaller than the diameter of the post 52 on the placement tool 14 in order to optimize the detachable interconnection thereof. In a most preferred embodiment of this invention, the diameter of the hole 30 is between about 0.030 and about 0.40 inch and the diameter of the post 52 is between about 0.055 and about 0.065 inch.

Furthermore it has been found that the post 52, preferably, ably, should have a minimum length of at least about 0.060 inch to assure retention of the tab 28 thereon. Additionally, it has been found that in order to most preferably position the hole 30 on the tab 28 for interconnection with the post 52, the hole 30 should be positioned beyond the longitudinal midpoint point between a proximal end 72 of the tab 28 mounted on the voice prosthesis device 12 and a distal end 74 of the tab 28 (FIG. 2) nearer to the distal end 74 thereof. Most preferably, the longitudinal distance of the hole 30 from the distal end 74 of tab 28 should be between about 0.035 and about 0.045 inch.

Figure 8:
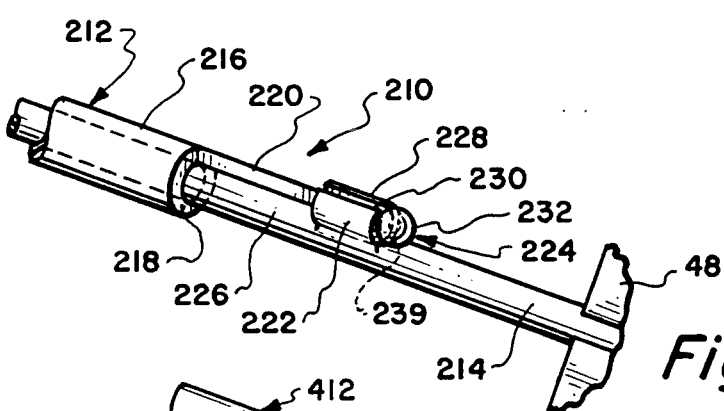
FIG. 8 is a partial perspective view illustrating another embodiment of an assembly in accordance with the present invention with a voice prosthesis device detachably interconnected with a placement tool.

Another embodiment of an assembly 210 in accordance with the present invention is shown in FIG. 8 wherein it can be seen that the assembly 210 includes a voice prosthesis device 212 detachably interconnected with a placement tool 214. Housing 216 of voice prosthesis device 212 includes, at its proximal end 218, a retention means in the form of an elongated rod-shaped tab 220. The tab 220 has an attachment means in the form of a mating section 222 on the tab 220 intermediate the end of the tab 220 mounted on the proximal end of the voice prosthesis device 212 and a distal end 224 of the tab 220 remote therefrom. The mating section 222 is adapted to interconnect with an attachment means on the placement end 226 of the placement tool 214. The attachment means on the tool 214 is in the form of a bracket or clip 228 having a groove 239 therein for accommodating and detachably interconnecting the tool 214 with mating section 222 on tab 220. A locking element 232 in the shape of a bead or ball or other compatible shape is provided at the distal end 224 of the tab 220 to enable a positive mechanical interlock between the elongated tab 220 and the placement tool 214 until detachment is desired after completion of the positioning of the voice prosthesis device 212.

Figure 9:
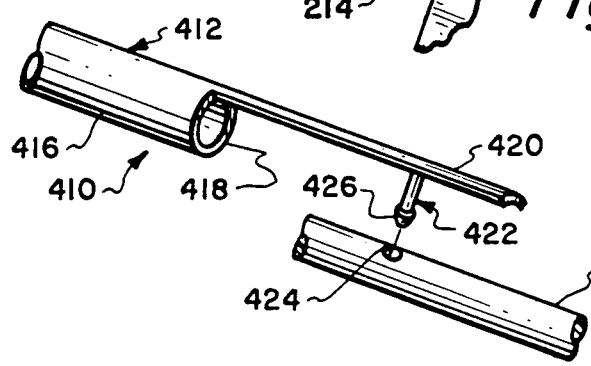
FIG. 9 is a partial perspective view illustrating another embodiment of an assembly in accordance with the present invention with a voice prosthesis device positioned to be detachably interconnected with a placement tool.

FIG. 9 shows another embodiment of an assembly 410 in accordance with the present invention illustrating a voice prosthesis device 412 in the process of being detachably interconnected with a placement tool 414. In this embodiment, the housing 416 of the voice prosthesis device 412 has at its proximal end 418, a tab 420 which includes an attachment means in the form of a post or protuberance 422. The post 422 adapted to detachably interconnect with an attachment means on the placement tool 414. As depicted in FIG. 9, the attachment means on the placement tool 414 is a hole 424 and the post 422 is dimensioned to nestingly fit into such hole 424 and to be detachably interconnected therewith until disengagement is desired. In order to assure a positive interlock of the voice prosthesis device 412 with tool 414 during positioning of the device 412, a locking element 426 is provided at the terminal end of the post 422. The shape of the element 426 is selected to enable positive engagement of the device 412 and the tool 414 during positioning and for detachment of these assembly parts when desired.

While preferred embodiments of the voice prosthesis insertion assemblies and their methods of operation have been shown and described above, persons skilled in the art will readily appreciate the various changes and modifications that may be made without departing from the spirit and scope of the present invention, which is defined in the following claims.

We claim:

1. A voice prosthesis insertion assembly comprising a voice prosthesis device and a placement tool for positioning said device in a fistula connecting a trachea and an esophagus of a patient, said voice prosthesis device having first attachment means formed thereon and said placement tool having second attachment means molded integrally and homogeneously thereon for detachably joining said first attachment means on said device with said second attachment means on said tool during positioning of said device in said fistula wherein said voice prosthesis device includes a longitudinally extending housing with a tab projecting radially outwardly therefrom, said first attachment means on said voice prosthesis device comprising a hole formed on said tab, and said second attachment means on said tool comprising a post molded integrally and homogeneously thereon, said post being structured and dimensioned to interconnect with said hole.

2. The assembly of claim 1 wherein said post on said tool includes an attachment section at the terminal end thereof remote from said housing, said attachment section being shaped to provide a positive interlock with said hole on said tab.

3. A voice prosthesis insertion assembly comprising a voice prosthesis device and a placement tool for positioning said device in a fistula connecting a trachea and an esophagus of a patient, said voice prosthesis device and said placement tool having attachment means formed thereon and said placement tool having second means molded integrally and homogeneously thereon for interconnecting said first attachment means on said device with said second attachment means on said tool during position of said device in said fistula wherein said first attachment means comprises a mating section formed on said voice prosthesis device, and said second attachment means comprises a reciprocal mating section formed on said placement tool adapted for detachable joinder of said device and said tool; and wherein said voice prosthesis device includes a longitudinally extending housing with a rod shaped tab projecting radially outwardly therefrom, said rod shaped tab including said mating section thereon, and said reciprocal mating section on said tool comprising a bracket having a groove therein adapted to interconnect with said mating section on said rod shaped tab.

4. A voice prosthesis insertion assembly comprising a voice prosthesis device and a placement tool for positioning said device in a fistula connecting a trachea and an esophagus of a patient, said voice prosthesis device and said placement tool having attachment means formed thereon and said placement tool having second means molded integrally and homogeneously thereon for interconnecting said first attachment means on said device with said second attachment means on said tool during positioning of said device in said fistula;

wherein said first attachment means comprises a mating section formed on said voice prosthesis device, and said second attachment means comprises a reciprocal mating section formed on said placement tool adapted for detachable joinder of said device and said tool; and wherein said voice prosthesis device includes a longitudinally extending housing with a tab projecting radially outwardly therefrom, said mating section on said voice prosthesis device comprising a post formed on said tab, and said reciprocal mating section on said tool comprising a hole formed therein, said post on said tab being adapted to interconnect with said hole in said tool.

5. The assembly of claim 4 wherein said post on said tab includes an attachment section at the terminal end there, said attachment section being shaped to provide a positive interlock with said hole in said tool.

6. In an assembly including, in combination:
a voice prosthesis device; and
a placement tool for positioning said voice prosthesis device in a fistula connection a tracheostoma and a esophagus of a patient;
said voice prosthesis device including a housing with a channel therein for permitting the passage of air from the trachea to the esophagus, said housing having a proximal end with a retention means mounted thereon and projecting radially outwardly therefrom, a distal end extending into the esophagus and a valve means positioned within the housing for controlling the passage of air through the channel in the housing;
said placement tool including an elongated housing having a handle at a first end thereof and a placement portion on a second end opposite said first end, said placement portion being shaped for insertion within the cylindrical housing of the voice prosthesis device to position said device in said fistula of said patient; the improvement comprising:
including a first attachment means on said retention means of said voice prosthesis device and a second attachment means molded integrally and homogeneously on said placement tool intermediate said first and second ends thereof, said first and second attachment means detachably interconnecting said voice prosthesis device with said placement tool during positioning of said device in said fistula; and
wherein said retention means is a tab and said first attachment means on said retention means is a hole formed in said tab, said second attachment means on said placement tool is a post formed on said tool, said post being adapted to engage with said hole in said tab to provide said detachable interconnection of said voice prosthesis device and said placement tool; and
wherein said hole in said tab is reinforced by thickening the cross-sectional dimension of the tab adjacent the circumference of said hole.

7. The assembly of claim 6 wherein said attachment means for detachably interconnecting said voice prosthesis device with said placement tool comprises a mating section formed on said retention means and a reciprocal mating section formed on said placement tool.

8. The assembly of claim 6 in which the tab is formed of stretchable material and wherein said hole in said tab in the unstretched condition is of a diameter smaller than the diameter of said post.

9. The assembly of claim 8 wherein the diameter of said hole is between about 0.030 and 0.040 inch and the diameter of said post is between about 0.055 and 0.065 inch.

10. The assembly of claim 6 wherein said cross-section of said tab is thickened by between about 0.01 and 0.015 inch adjacent said hole.

11. In an assembly including, in combination:
a voice prosthesis device; and
a placement tool for positioning said voice prosthesis device in a fistula connection a tracheostoma and an esophagus of a patient;
said voice prosthesis device including a housing with a channel therein for permitting the passage of air from the trachea to the esophagus, said housing having a proximal end with a retention means mounted thereon and projecting radially outwardly therefrom, a distal end extending into the esophagus and a valve means positioned within the housing for controlling the passage of air through the channel in the housing;
said placement tool including an elongated housing having a handle at a first end thereof and a placement portion on a second end opposite said first end, said placement portion being shaped for insertion within the cylindrical housing of the voice prosthesis device to position said device in said fistula of said patient; the improvement comprising:
including a first attachment means on said retention means of said voice prosthesis device and a second attachment means molded integrally and homogeneously on said placement tool intermediate said first and second ends thereof, said first and second attachment means detachably interconnecting said voice prosthesis device with said placement tool during positioning of said device in said fistula;
said retention means is a tab and said first attachment means on said retention means is a hole formed in said tab, said second attachment means on said placement tool is a post formed on said tool, said post being adapted to engage with said hole in said tab to provide said detachable interconnection of said voice prosthesis device and said placement tool; and
wherein said tab has a proximal end and a distal end spaced longitudinally therefrom, said proximal end of said tab is mounted on said voice prosthesis device and said hole in said tab is positioned beyond the longitudinal midpoint between the proximal and distal ends of the tab nearer to the distal end thereof.

12. The assembly of claim 11 wherein said hole in said tab is positioned a distance of between about 0.035 and 0.045 inch from the distal end of said tab.

13. The assembly of claim 6 wherein the length of said post is at least 0.60 inch.

14. In a voice prosthesis insertion assembly formed of a voice prosthesis device and a placement tool for positioning the device in a fistula connecting the trachea and the esophagus of a patient the improvement comprising:
cooperative latching means formed of a post mounted on the insertion tool and a hole formed in an elastomeric tab connected to the device for being latched onto the post; and
reinforcing means on said tab adjacent said hole for preventing tearing of the tab.

15. An assembly according to claim 14 in which the post is cylindrical and the diameter of the post is larger than the diameter of the hole in the tab.

16. An assembly according to claim 15 in which the post has an enlarged head portion.

17. An assembly according to claim 16 in which the region of the tab surrounding the hole is thicker than the remainder of the tab to provide said reinforcement.

18. An assembly according to claim 17 wherein said region surrounding the hole in the tab is thickened by between about 0.010 and about 0.015 inch.

* * * * *